United States Patent
Duan (10) Patent No.: US 11,453,653 B2
(45) Date of Patent: Sep. 27, 2022

(54) PROCESS FOR SEPARATING CARBON DIOXIDE AND ARGON FROM HYDROCARBONS

(71) Applicant: SABIC GLOBAL TECHNOLOGIES B.V., Bergen op Zoom (NL)

(72) Inventor: Jintang Duan, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/259,979

(22) PCT Filed: Jun. 17, 2019

(86) PCT No.: PCT/IB2019/055065
§ 371 (c)(1),
(2) Date: Jan. 13, 2021

(87) PCT Pub. No.: WO2020/012268
PCT Pub. Date: Jan. 16, 2020

(65) Prior Publication Data
US 2021/0284616 A1    Sep. 16, 2021

Related U.S. Application Data

(60) Provisional application No. 62/697,799, filed on Jul. 13, 2018.

(51) Int. Cl.
*C07D 301/08* (2006.01)
*C07D 303/04* (2006.01)

(52) U.S. Cl.
CPC ......... *C07D 301/08* (2013.01); *C07D 303/04* (2013.01)

(58) Field of Classification Search
CPC ............................ C07D 301/08; C07D 303/04
(Continued)

(56) References Cited

U.S. PATENT DOCUMENTS

| 4,879,396 A | 11/1989 | Ozero |
| 4,904,807 A | 2/1990 | Ozero |

(Continued)

FOREIGN PATENT DOCUMENTS

| CN | 106631667 | 5/2017 |
| EP | 0200518 | 11/1986 |

(Continued)

OTHER PUBLICATIONS

Wikipedia, Vapor-;liquid separator, Nov. 2017, p. 1-4. (Year: 2017).*

(Continued)

*Primary Examiner* — Taylor V Oh
(74) *Attorney, Agent, or Firm* — Norton Rose Fulbright US LLP (57) ABSTRACT

Systems and methods for producing ethylene oxide (EO) are disclosed. Ethylene oxide is produced by direct oxidizing ethylene with oxygen in a reactor. The effluent from the reactor is processed to produce (a) a product stream comprising water and ethylene oxide, (b) a reabsorber overhead stream comprising ethylene, methane, argon, and carbon dioxide, and (c) a carbonate flash gas stream comprising carbon dioxide, ethylene, methane, and water. The reabsorber overhead stream and the carbonate flash gas stream are combined to form a reclaim gas stream. The reclaimed gas stream is separated in a membrane separation unit to remove carbon dioxide and argon, forming a recycle stream comprising primarily ethylene and methane, collectively.

19 Claims, 3 Drawing Sheets

(58) Field of Classification Search
USPC .......................................................... 549/523
See application file for complete search history.

(56) References Cited

U.S. PATENT DOCUMENTS

| | | |
|---|---|---|
| 5,817,841 A | 10/1998 | Baker et al. |
| 2011/0245518 A1* | 10/2011 | Hirota .................. B01J 37/0213 |
| | | 549/534 |

FOREIGN PATENT DOCUMENTS

| | | | |
|---|---|---|---|
| EP | 373683 | 6/1990 | |
| EP | 0893443 | 1/1999 | |
| WO | WO 1995/008545 | 3/1995 | |
| WO | WO-2014184751 A1 * | 11/2014 | ........... C07D 301/08 |

OTHER PUBLICATIONS

Bernardo, et al. "Integrated membrane operations in the ethylene oxide production," *Clean Technologies and Environmental Policy*, 2011, 14(3):475-485.
International Search Report and Written Opinion issued in International Patent Application No. PCT/IB2019/055065, dated Oct. 22, 2019.

* cited by examiner

PROCESS FOR SEPARATING CARBON DIOXIDE AND ARGON FROM HYDROCARBONS

CROSS REFERENCE TO RELATED APPLICATIONS

This application is a national phase under 35 U.S.C. § 371 of International Application No. PCT/IB2019/055065, filed Jun. 17, 2019, which claims the benefit of priority to U.S. Provisional Patent Application No. 62/697,799, filed Jul. 13, 2018, the entire contents of each of which are hereby incorporated by reference in their entirety.

FIELD OF INVENTION

The present invention generally relates to methods of producing ethylene oxide. More specifically, the present invention relates to ethylene oxide production methods that include directly oxidizing ethylene to produce ethylene oxide and purifying unreacted ethylene by removing carbon dioxide and argon with a membrane separation unit.

BACKGROUND OF THE INVENTION

Ethylene oxide (EO) is used as an intermediate for many organic synthesis processes. For example, ethylene oxide is a raw material used to produce ethylene glycols, including, monoethylene glycol, diethylene glycol, triethylene glycol, and polyethylene glycols. Monoethylene glycol is an antifreeze and coolant for engines and intermediate for producing polyester fibers and plastic bottles. Diethylene glycol can be used to produce polyurethanes, plasticizers, and organic solvents. Triethylene glycols are often used as plasticizers and moisture-retaining agents. Polyethylene glycols are used in perfumes, cosmetics, lubricants, and plasticizers.

In the chemical industry, ethylene oxide is generally produced by direct oxidation of ethylene. By-products of this process include carbon dioxide, which is mixed with unreacted ethylene and other diluent and impurities such as argon. To reduce production cost of ethylene oxide, unreacted ethylene is generally separated from carbon dioxide and argon and then recycled to the reactor. Conventionally, the separation of carbon dioxide from unreacted ethylene is carried out using metal carbonates, such as potassium carbonate in a carbon dioxide scrubber. The potassium carbonate reacts with water and carbon dioxide to form potassium bicarbonate. A large amount of steam is then used to regenerate potassium carbonate from potassium bicarbonate, resulting in high energy consumption. Argon is usually removed from ethylene by bleeding it off, which results in loss of unreacted ethylene.

Overall, while methods of producing ethylene oxide exist, the need for improvements in this field persists in light of at least the aforementioned drawbacks of the conventional methods.

BRIEF SUMMARY OF THE INVENTION

A solution to at least some of the above-mentioned problems associated with the production process for ethylene oxide has been discovered. The solution resides in a method of producing ethylene oxide that uses a membrane separation unit to separate carbon dioxide and argon from unreacted ethylene. Notably, the method is capable of reducing energy consumption for the ethylene oxide production process because the membrane separation unit does not consume a large amount of energy as compared to the $CO_2$ absorption process used in the conventional methods. Additionally, the membrane separation unit separates argon along with carbon dioxide from unreacted ethylene. Thus, it avoids loss of ethylene during argon bleeding, which is used in the conventional methods for producing ethylene oxide. Therefore, the method of the present invention provides a technical solution over at least some of the problems associated with the currently available production processes for ethylene oxide mentioned above.

Embodiments of the invention include a method of producing ethylene oxide. The method comprises reacting ethylene with a gas comprising oxygen in a reactor to produce a reactor effluent comprising ethylene oxide, carbon dioxide, unreacted ethylene, oxygen, methane and argon. The method further comprises processing the reactor effluent to produce (a) a product stream comprising 5 to 15 wt. % ethylene oxide, (b) a reabsorber overhead stream comprising 20 to 40 wt. % ethylene and 10 to 30 wt. % methane, 1 to 10 wt. % argon, and 30 to 50 wt. % carbon dioxide and (c) a carbonate flash gas stream comprising 25 to 50 wt. % carbon dioxide, 5 to 15 wt. % ethylene, 5 wt. % to 10 wt. % methane, and 40% to 60% water. The method further comprises combining the reabsorber overhead stream and the carbonate flash gas stream to produce a reclaim gas stream. The method further still comprises removing carbon dioxide and argon from the reclaim gas stream, by a membrane separation unit to form a (1) recycle gas stream comprising ethylene and methane and (2) a gas stream comprising the removed carbon dioxide and the removed argon. The method further still comprises flowing the recycle gas stream to the reactor.

Embodiments of the invention include a method of producing ethylene oxide. The method comprises reacting ethylene with a gas comprising oxygen in a reactor to produce a reactor effluent comprising ethylene oxide, carbon dioxide, unreacted ethylene, oxygen, methane and argon. The method further includes processing the reactor effluent in an ethylene oxide (EO) absorber to produce (A) an aqueous stream comprising 2 to 5 wt. % ethylene oxide and 2 to 5 wt. % monoethylene glycol and (B) an EO absorber overhead stream comprising 2 to 15 wt. % carbon dioxide, 20 to 35 wt. % ethylene, and 30 to 45 wt. % methane. The method further includes processing the aqueous stream to produce (a) a product stream comprising 5 to 15 wt. % ethylene oxide, (b) a reabsorber overhead stream comprising 20 to 40 wt. % ethylene, 10 to 30 wt. % methane, 1 to 10 wt. % argon, and 30 to 50 wt. % carbon dioxide. The method further includes processing the EO absorber overhead stream to produce a carbonate flash gas stream comprising 25 to 50 wt. % carbon dioxide, 5 to 15 wt. % ethylene, 5 to 10 wt. % methane and 40 to 60 wt. % water. The method further includes combining the reabsorber overhead stream and the carbonate flash gas stream to produce a reclaim gas stream. The method further still includes removing carbon dioxide and argon from the reclaim gas stream, by a membrane separation unit to form (1) a recycle gas stream comprising ethylene and methane and (2) a gas stream comprising the removed carbon dioxide and the removed argon. The method further still comprises flowing the recycle gas stream to the reactor.

Embodiments of the invention include a method of producing ethylene oxide. The method comprises reacting ethylene with a gas comprising oxygen in a reactor to produce a reactor effluent comprising ethylene oxide, carbon dioxide, unreacted ethylene, oxygen, methane and argon. The method further includes processing the reactor effluent in an ethylene oxide (EO) absorber to produce (A) an aqueous stream comprising 2 to 5 wt. % ethylene oxide and 2 to 5 wt. % monoethylene glycol and (B) an EO absorber overhead stream comprising 2 to 15 wt. % carbon dioxide, 20 to 35 wt. % ethylene, and 30 to 45 wt. % methane. The method further includes processing the aqueous stream to produce (a) a product stream comprising 5 to 15 wt. % ethylene oxide, (b) a reabsorber overhead stream comprising 20 to 40 wt. % ethylene, 10 to 30 wt. % methane, 1 to 10 wt. % argon, and 30 to 50 wt. % carbon dioxide. The method further includes processing the EO absorber overhead stream to produce a carbonate flash gas stream comprising 25 to 50 wt. % carbon dioxide, 5 to 15 wt. % ethylene, 5 to 10 wt. % methane and 40 to 60 wt. % water. The method further includes combining the reabsorber overhead stream and the carbonate flash gas stream to produce a reclaim gas stream. The method further still includes removing carbon dioxide and argon from the reclaim gas stream, by a membrane separation unit to form (1) a recycle gas stream comprising ethylene and methane and (2) a gas stream comprising the removed carbon dioxide and the removed argon. The membrane separation unit comprises hollow fiber membrane separation unit, spiral-wound membrane separation unit, or combinations thereof. The method further still comprises flowing the recycle gas stream to the reactor.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Conventionally, ethylene oxide is produced via direct oxidation of ethylene in a reactor. Carbon dioxide byproduct and argon impurity are separated from unreacted ethylene via metal carbonate absorption and argon bleeding, respectively. However, the regeneration of the reacted metal carbonate consumes a large amount of energy, resulting in high production cost for ethylene oxide. Furthermore, argon bleeding often results in loss of unreacted ethylene in the separation process, thereby further increasing the production cost for ethylene oxide. The present invention provides a solution to at least some of the problems. The solution is premised on a method of producing ethylene oxide that includes using membrane separation unit to separate both carbon dioxide and argon from unreacted ethylene. The membrane unit can be reused, and overall, the use of the membrane separation unit does not consume a large amount of energy as compared to the regeneration of metal carbonate used in the conventional methods. Argon is removed by the membrane separation unit along with carbon dioxide with little or no loss of unreacted ethylene. Therefore, overall, the method of the present invention can reduce the production cost for ethylene oxide compared to conventional methods. These and other non-limiting aspects of the present invention are discussed in further detail in the following section.

A. Systems for Producing Ethylene Oxide

Figure 1A:
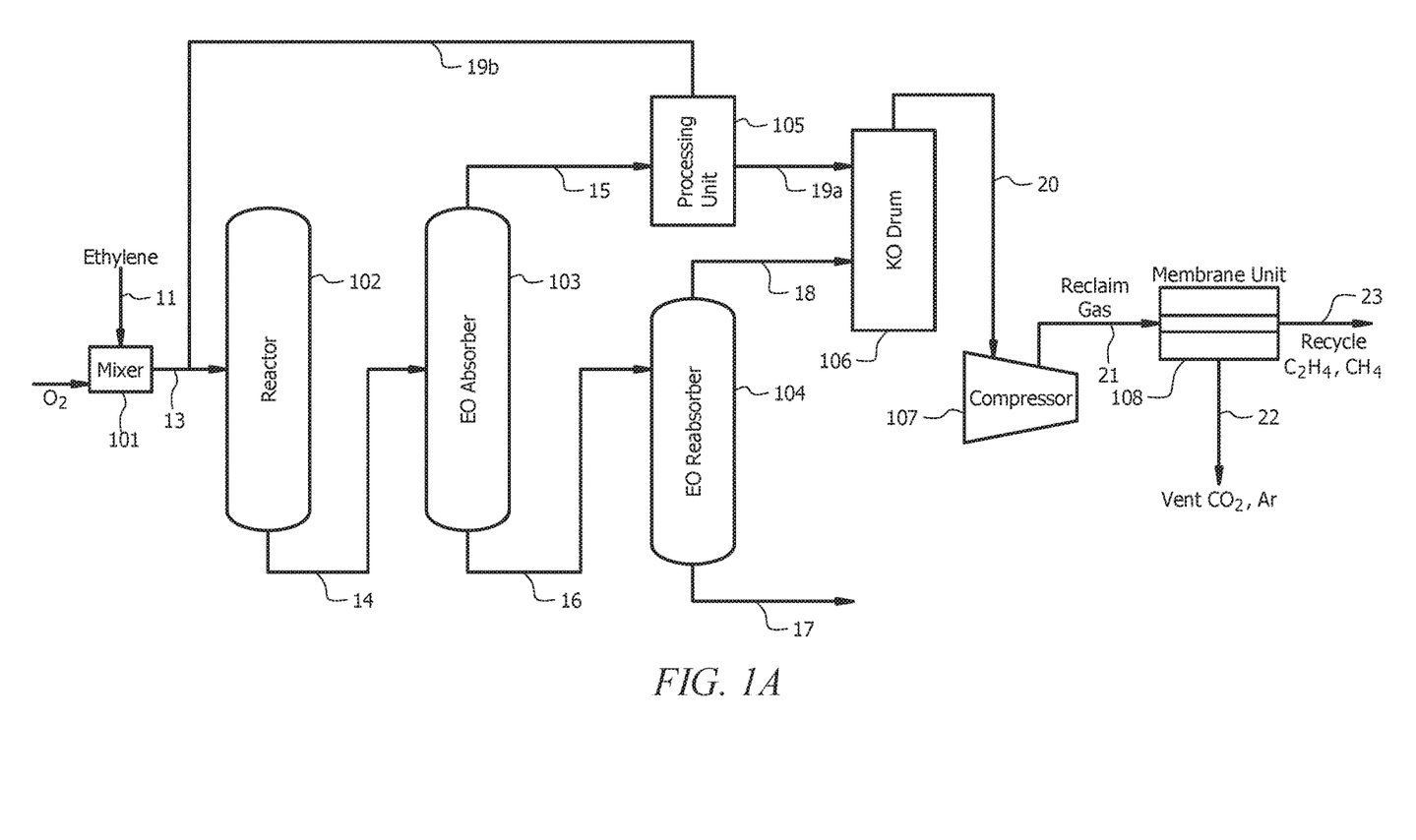
FIG. 1A shows a schematic diagram of a system for producing ethylene oxide, according to embodiments of the invention.

In embodiments of the invention, the system for producing ethylene oxide can include a reactor and an integrated separation system for purifying the ethylene oxide and recycling unreacted ethylene back to the reactor. With reference to FIG. 1A, a schematic diagram is shown of ethylene oxide production system 100 for producing ethylene oxide (EO) with lower production cost than a conventional EO production method. According to embodiments of the invention, ethylene oxide production system 100 may include feed mixer 101 configured to receive and mix feed ethylene stream 11 and oxidative gas stream 12 to form feed stream 13. In embodiments of the invention, oxidative gas stream 12 comprises 98.00 to 99.99 wt. % oxygen ($O_2$), 0.01 to 0.50 wt. % argon (Ar), 0.01 to 1.50 wt. % nitrogen ($N_2$), or combinations thereof.

In embodiments of the invention, an outlet of feed mixer 101 may be in fluid communication with an inlet of EO reactor 102 such that feed stream 13 flows from feed mixer 101 to EO reactor 102. In embodiments of the invention, EO reactor 102 may include a catalyst bed comprising a catalyst for oxidizing ethylene. The catalyst may include Ag supported on alumina, silica, or combinations thereof. In embodiments of the invention, EO reactor 102 includes a fixed bed reactor. In embodiments of the invention, EO reactor 102 may be configured to react ethylene with oxygen in the presence of the catalyst to produce effluent stream 14. In embodiments of the invention, effluent stream 14 may include ethylene oxide, carbon dioxide, and unreacted ethylene, oxygen, methane, and argon.

In embodiments of the invention, an outlet of EO reactor 102 may be in fluid communication with an inlet of EO absorber 103 such that effluent stream 14 flows from EO reactor 102 to EO absorber 103. According to embodiments of the invention, EO absorber 103 is configured to separate ethylene oxide from effluent stream 14 to form EO absorber overhead stream 15 and aqueous stream 16. In embodiments of the invention, EO absorber 103 comprises a wet scrubber. EO absorber overhead stream 15 may include carbon dioxide, ethylene, methane, or combinations thereof. Aqueous stream 16 may include ethylene oxide, monoethylene glycol, water, or combinations thereof.

According to embodiments of the invention, EO absorber 103 comprises a bottom outlet in fluid communication with an inlet of EO reabsorber 104 such that aqueous stream 16 flows from EO absorber 103 to EO reabsorber 104. In embodiments of the invention, there may be an EO stripper between EO absorber 103 and EO reabsorber 104. Stream 16 may first flow to EO stripper and the overhead vapor from the EO stripper may flow to EO reabsorber 104 to form product stream 17 and reabsorber overhead stream 18. In embodiments of the invention, the EO stripper and EO reabsorber 104 may be configured to separate aqueous stream 16 to form (A) product stream 17 comprising ethylene oxide and water and (B) reabsorber overhead stream 18 comprising ethylene, methane, argon, carbon dioxide, or combinations thereof. In embodiments of the invention, non-limiting examples of EO reabsorber 104 include a packed column where EO contacts with a water absorbent. In embodiments of the invention, EO reabsorber 104 comprises a top outlet in fluid communication with a first inlet of knockout drum 106 such that reabsorber overhead stream 18 flows from EO reabsorber 104 to knockout drum 106. EO reabsorber 104 may further comprise a bottom outlet configured to release product stream 17 therefrom.

According to embodiments of the invention, EO absorber 103 comprises a top outlet in fluid communication with an inlet of processing unit 105 such that EO absorber overhead stream 15 flows from EO absorber 103 to processing unit 105. In embodiments of the invention, processing unit 105 is configured to remove at least some carbon dioxide, methane, and/or ethylene from EO absorber overhead stream 15 to produce carbonate flash gas stream 19a comprising primarily carbon dioxide, ethylene, methane, and water, collectively and first recycle stream 19b comprising primarily ethylene and methane, collectively.

Figure 1B:
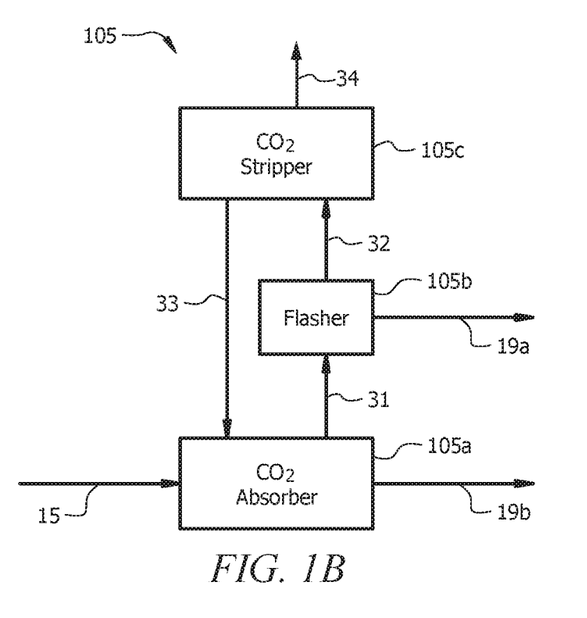
FIG. 1B shows a schematic diagram of a processing unit used in a system for producing ethylene oxide, according to embodiments of the invention.

In embodiments of the invention, as shown in FIG. 1B, processing unit 105 includes carbon dioxide absorber 105a configured to absorb at least some carbon dioxide from EO absorber overhead stream 15 to form (1) first recycle stream 19b comprising primarily ethylene and methane, collectively and (2) rich carbonate solution stream 31 comprising metal carbonate and bicarbonate, water, dissolved carbon dioxide, ethylene and methane. According to embodiments of the invention, carbon dioxide absorber 105a comprises a first outlet in fluid communication with an inlet EO reactor 102 such that first recycle stream 19b flows from carbon dioxide absorber 105a to EO reactor 102. In embodiments of the invention, first recycle stream 19b may be flowed to a mixer before it is flowed back to EO reactor 102. Carbon dioxide absorber 105a may comprise a second outlet in fluid communication with flasher 105b such that rich carbonate solution stream 31 flows from carbon dioxide absorber 105a to flasher 105b. According to embodiments of the invention, flasher 105b may be configured to separate rich carbonate solution stream 31 to form carbonate flash gas stream 19a comprising primarily carbon dioxide, ethylene, methane, and water collectively and residual stream 32 comprising primarily metal bicarbonate, metal carbonate and water. In embodiments of the invention, flasher 105b comprises a first outlet in fluid communication with a second inlet of knockout drum 106 such that carbonate flash gas stream 19a flows from processing unit 105 (flasher 105b) to knockout drum 106. Flasher 105b may comprise a second outlet in fluid communication with carbon dioxide stripper 105c such that residual stream flows from flasher 105b to stripper 105c. Carbon dioxide stripper 105c may be configured to remove at least some of carbon dioxide from residual stream 32 to form lean carbonate solution stream 33. An outlet of carbon dioxide stripper 105c may be in fluid communication with an inlet of carbon dioxide absorber 105a such that lean carbonate solution stream 33 flows from carbon dioxide stripper 105c to carbon dioxide absorber 105a. In embodiments of the invention, lean carbonate solution stream 33 may include 10 to 20 wt. % metal carbonate, 10 to 20 wt. % metal bicarbonate and 60 to 80 wt. % water. Carbon dioxide stripper 105c may include a $CO_2$ vent such that $CO_2$ vent stream 34 can be vented from carbon dioxide stripper 105c.

According to embodiments of the invention, knockout drum 106 is configured to remove water from a combined stream of reabsorber overhead stream 18 and carbonate flash gas stream 19a to form de-watered stream 20. In embodiments of the invention, knockout drum comprises an outlet in fluid communication with an inlet of compressor 107 such that de-watered stream 20 flows from knockout drum 20 to compressor 107. In embodiments of the invention, compressor 107 is configured to compress de-watered stream 20 to form reclaim gas stream 21. Reclaim gas stream 21 may comprise primarily carbon dioxide, ethylene, argon, and methane.

In embodiments of the invention, an outlet of compressor 107 is in fluid communication with an inlet of membrane separation unit 108 such that reclaim gas stream flows from compressor 107 to membrane separation unit 108. According to embodiments of the invention, membrane separation unit 108 is configured to separate reclaim gas stream 21 to form (I) vent stream 22 comprising primarily carbon dioxide and argon and (II) second recycle stream 23 (recycle gas stream) comprising primarily ethylene and methane. In embodiments of the invention, membrane separation unit 108 comprises hollow fiber membrane separation unit, spiral-wound membrane separation unit, or combinations thereof. Membrane separation unit 108 may include one or more membrane modules, one or more housing pressure vessels, one or more compressors. In embodiments of the invention, membrane separation unit 108 may include a first outlet in fluid communication with at least one of an inlet of EO reactor 102, an inlet of EO absorber 103, and an inlet of carbon dioxide absorber 105a such that second recycle stream 23 flows from membrane separation unit 108 to one or more of EO reactor 102, EO absorber 103, and carbon dioxide absorber 105a.

B. Methods of Producing Ethylene Oxide

Figure 2:
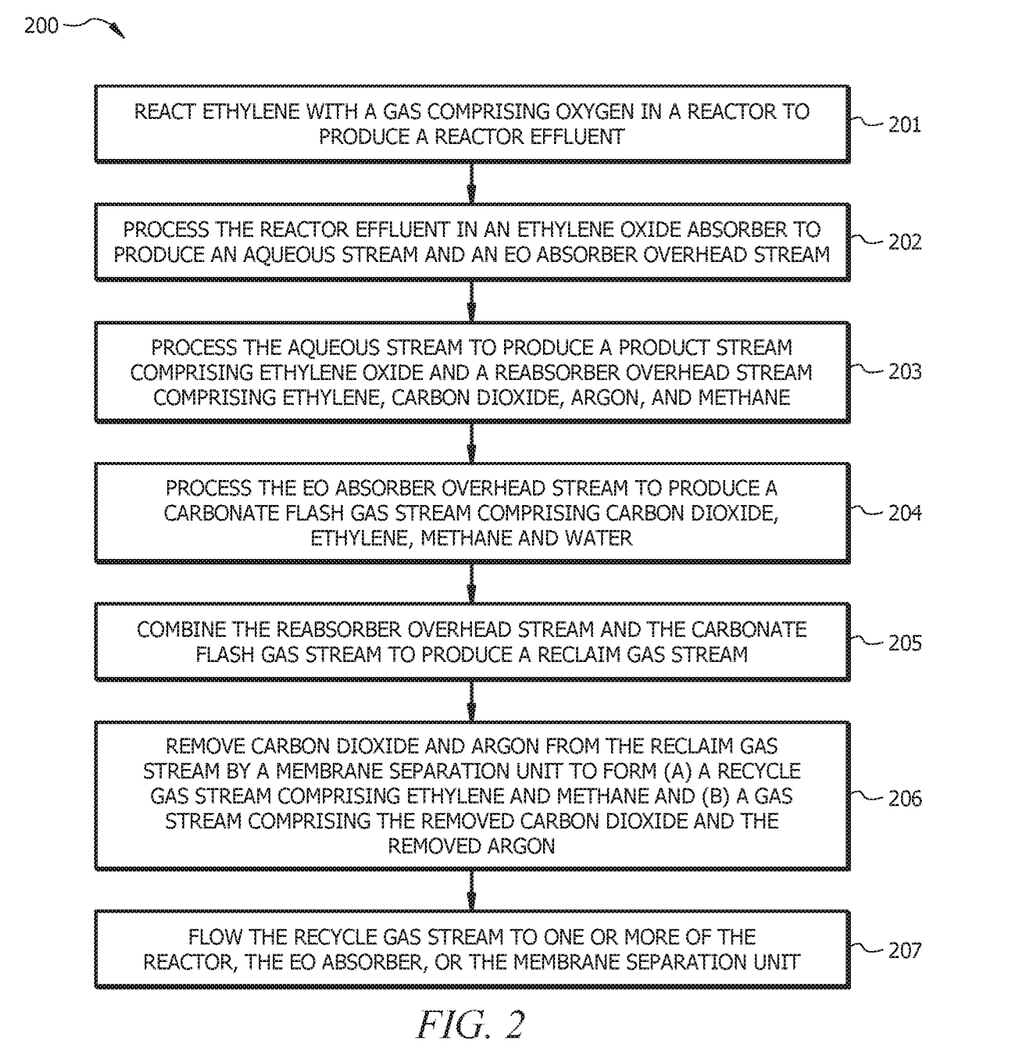
FIG. 2 shows a schematic flow chart for a method of producing ethylene oxide, according to embodiments of the invention.

As shown in FIG. 2, embodiments of the present invention include method 200 of producing ethylene oxide. Method 200 may be implemented by ethylene oxide production system 100, as shown in FIG. 1A. According to embodiments of the invention, as shown in block 201, method 200 comprises reacting ethylene (of feed ethylene stream 11) with a gas (oxidative gas stream 12) comprising oxygen in EO reactor 102 to produce a reactor effluent (effluent stream 14). In embodiments of the invention, oxidative gas stream 12 may include 98.00 to 99.99 wt. % oxygen ($O_2$), 0.01 to 0.50 wt. % argon (Ar), 0.01 to 1.50 wt. % nitrogen ($N_2$). Feed ethylene stream 11 and oxidative gas stream 12 may be mixed in mixer 101 to form feed stream 13 for EO reactor 102. In embodiments of the invention, the weight ratio of $O_2$ to ethylene in feed stream 13 is in a range of 0.2 to 0.5 and all ranges and values there between including ranges of 0.2 to 0.22, 0.22 to 0.24, 0.24 to 0.26, 0.26 to 0.28, 0.28 to 0.30, 0.30 to 0.32, 0.32 to 0.34, 0.34 to 0.36, 0.36 to 0.038, 0.38 to 0.40, 0.40 to 0.42, 0.42 to 0.44, 0.44 to 0.46, 0.46 to 0.48, and 0.48 to 0.50. According to embodiments of the invention, effluent stream 14 comprises ethylene oxide, carbon dioxide, and unreacted ethylene, oxygen, methane and argon.

In embodiments of the invention, the reacting of block 201 is carried out under reaction conditions including a reaction temperature of 200 to 300° C. and all ranges and values there between including ranges of 200 to 205° C., 205 to 210° C., 210 to 215° C., 215 to 220° C., 220 to 225° C., 225 to 230° C., 230 to 235° C., 235 to 240° C., 240 to 245° C., 245 to 250° C., 250 to 255° C., 255 to 260° C., 260 to 265° C., 265 to 270° C., 270 to 275° C., 275 to 280° C., 280 to 285° C., 285 to 290° C., 290 to 295° C., and 295 to 300° C. The reaction conditions in block 201 may further include a reaction pressure of 10 to 35 bar and all ranges and values there between including ranges of 10 to 11 bar, 11 to 12 bar, 12 to 13 bar, 13 to 14 bar, 14 to 15 bar, 15 to 16 bar, 16 to 17 bar, 17 to 18 bar, 18 to 19 bar, 19 to 20 bar, 20 to 21 bar, 21 to 22 bar, 22 to 23 bar, 23 to 24 bar, 24 to 25 bar, 25 to 26 bar, 26 to 27 bar, 27 to 28 bar, 28 to 29 bar, 29 to 30 bar, 30 to 31 bar, 31 to 32 bar, 32 to 33 bar, 33 to 34 bar, and 34 to 35 bar. According to embodiments of the invention, the reacting in block 201 is carried out in the presence of a catalyst. The catalyst may include silver supported on alumina, silica, silica-alumina, or combinations thereof. In embodiments of the invention, the reaction conditions in block 201 further include a gas hourly space velocity (GHSV) in a range of 3000 to 20000 $hr^{-1}$ and all ranges and values there between including ranges of 3000 to 4000 $hr^{-1}$, 4000 to 5000 $hr^{-1}$, 5000 to 6000 $hr^{-1}$, 6000 to 7000 $hr^{-1}$, 7000 to 8000 $hr^{-1}$, 8000 to 9000 $hr^{-1}$, 9000 to 10000 $hr^{-1}$, 10000 to 11000 $hr^{-1}$, 11000 to 12000 $hr^{-1}$, 12000 to 13000 $hr^{-1}$, 13000 to 14000 $hr^{-1}$, 14000 to 15000 $hr^{-1}$, 15000 to 16000 $hr^{-1}$, 16000 to 17000 $hr^{-1}$, 17000 to 18000 $hr^{-1}$, 18000 to 19000 $hr^{-1}$, and 19000 to 20000 $hr^{-1}$.

In embodiments of the invention, method 200 further includes processing effluent stream 14 in EO absorber 103 to produce aqueous stream 16 and EO absorber overhead stream 15, as shown in block 202. In embodiments of the invention, the processing in block 202 includes, in EO absorber 103, scrubbing ethylene oxide from effluent stream 14 with water. In embodiments of the invention, aqueous stream 16 includes 2 to 5 wt. % ethylene oxide, 2 to 5% monoethylene glycol, 0.01 to 0.10 wt. % ethylene, 0.01 to 0.05 wt. % argon, 0.01 to 0.05 wt. % methane, and 90 to 96 wt. % water. EO absorber overhead stream 15 may include 2 to 15 wt. % carbon dioxide, 20 to 35 wt. % ethylene, and 30 to 45 wt. % methane.

In embodiments of the invention, as shown in block 203, method 200 further includes processing aqueous stream 16 to produce (a) product stream 17 comprising ethylene oxide and (b) reabsorber overhead stream 18 comprising ethylene, methane, argon, and carbon dioxide. In embodiments of the invention, the processing in block 203 is carried out in EO reabsorber 104. In embodiments of the invention, aqueous stream 16 may flow to an EO stripper to produce an overhead stream and a bottom cycle water stream. The overhead stream containing EO, ethylene, methane, argon, and carbon dioxide may flow to EO reabsorber 104 to produce product stream 17 and reabsorber overhead stream 18. In embodiments of the invention, product stream 17 is an aqueous stream comprising 5 to 15 wt. % ethylene oxide and all ranges and values there between. In embodiments of the invention, product stream 17 further comprises a trace amount (less than 0.1 wt. %) of carbon dioxide. According to embodiments of the invention, reabsorber overhead stream 18 comprises 20 to 50 wt. % ethylene, 10 to 30 wt. % methane, 1 to 10 wt. % argon, and 20 to 50 wt. % carbon dioxide. In embodiments of the invention, product stream 17 may be in communication with an EG reactor to produce glycols. Additionally or alternatively, the product stream 17 can be further purified to produce high purity EO product in a purification column.

According to embodiments of the invention, as shown in block 204, method 200 further includes processing EO absorber overhead stream 15 in processing unit 105 to produce carbonate flash gas stream 19a and first recycle stream 19b. In embodiments of the invention, carbonate flash gas stream 19a comprises 10 to 50 wt. % carbon dioxide, 5 to 45 wt. % ethylene, 5 to 10 wt. % methane, and 40 to 60 wt. % water. First recycle stream 19b may comprise 20 to 45 wt. % ethylene, 20 to 50 wt. % methane, 1 to 15 wt. % carbon dioxide and 5 to 15 wt. % oxygen. In embodiments of the invention, carbonate flash gas stream 19a is flowed from flasher 105b to knock out drum 106. First recycle stream 19b may be flowed from carbon dioxide absorber 105a to EO reactor 102.

In embodiments of the invention, method 200 further includes combining reabsorber overhead stream 18 and carbonate flash gas stream 19a to produce reclaim gas stream 21, as shown in block 205. In embodiments of the invention, the combining in block 205 may include flowing reabsorber overhead stream 19a and carbonate flash gas stream to knock out drum 106 to form a combined stream. The combining in block 205 may further include removing water from the combined stream in knockout drum 106 to form de-watered stream 20. In embodiments of the invention, knockout drum 106 in block 205 may be operated under operating pressure of 0.05 to 2 bar and all ranges and values there between. Knockout drum 106 in block 205 may be operated at a temperature of 10 to 60° C. and all ranges and values there between. In embodiments of the invention, the combining in block 205 further includes compressing de-watered stream 20 in compressor 107 to form reclaim gas stream 21. In embodiments of the invention, the dewatered stream 20 is compressed to a pressure in a range of 15 to 50 bar and all ranges and values there between.

According to embodiments of the invention, as shown in block 206, method 200 further comprises removing carbon dioxide and argon from reclaim gas stream 21 by membrane separation unit 108, to form (1) second recycle gas stream 23 comprising ethylene and methane and (2) a gas stream (vent stream 22) comprising primarily the removed carbon dioxide and the removed argon. In embodiments of the invention, second recycle gas stream 23 comprises 40 to 70 wt. % ethylene and all ranges and values there between. In embodiments of the invention, membrane separation unit may comprise cellulose acetate/diacetate/triacetate membrane, polyimide membrane, perfluoro polymer membrane, polysulfone membrane, polycarbonate membrane, poly (phenylene oxide) membrane, or combinations thereof. In embodiments of the invention, membrane separation unit may be operated at an operating pressure in a range of 15 to 50 bar and all ranges and values there between including ranges of 15 to 16 bar, 16 to 18 bar, 18 to 20 bar, 20 to 22 bar, 22 to 24 bar, 24 to 26 bar, 26 to 28 bar, 28 to 30 bar, 30 to 32 bar, 32 to 34 bar, 34 to 36 bar, 36 to 38 bar, 38 to 40 bar, 40 to 42 bar, 42 to 44 bar, 44 to 46 bar, 46 to 48 bar, and 48 to 50 bar. In embodiments of the invention, as shown in block 207, method 200 further comprises flowing second recycle gas stream 23 to one or more of EO reactor 102, EO absorber 103, and carbon dioxide absorber 105a. In embodiments of the invention, the ethylene may be recycled to produce ethylene oxide in EO reactor 102.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, embodiments 1-17 are described. Embodiment 1 is a method of producing ethylene oxide. The method includes reacting ethylene with a gas containing oxygen in a reactor to produce a reactor effluent containing ethylene oxide, carbon dioxide, unreacted ethylene, oxygen, methane, and argon. The method also includes processing the reactor effluent to produce (a) a product stream containing 5 to 15 wt. % ethylene oxide, (b) a reabsorber overhead stream containing 20 to 50 wt. % ethylene and 10 to 30 wt. % methane, 1 to 10 wt. % argon, and 20 to 50 wt. % carbon dioxide and (c) a carbonate flash gas stream containing 10 to 50 wt. % carbon dioxide, 5 to 45 wt. % ethylene, 5% to 10 wt. % methane, and 40% to 60% water. The method further includes combining the reabsorber overhead stream and the carbonate flash gas stream to produce a reclaim gas stream, removing carbon dioxide and argon from the reclaim gas stream, by a membrane separation unit to form a (1) recycle gas stream containing ethylene and methane and (2) a gas stream containing the removed carbon dioxide and the removed argon, and flowing the recycle gas stream to the reactor. Embodiment 2 is the method of embodiment 1, wherein the reacting is carried out in the presence of a catalyst containing silver supported on alumina, silica, silica-alumina, or combinations thereof. Embodiment 3 is the method of either of embodiments 1 or 2, wherein the reacting is carried out at a reaction temperature of 200 to 300° C. Embodiment 4 is the method of any of embodiments 1 to 3, wherein the reacting is carried out at a reaction pressure of 10 to 35 bar. Embodiment 5 is the method of any of embodiments 1 to 4, wherein the processing includes: i) processing the reactor effluent in an ethylene oxide (EO) absorber to produce (A) an aqueous stream containing 2 to 5 wt. % ethylene oxide, 2 to 5 wt. % monoethylene glycol and (B) an EO absorber overhead stream containing 2 to 15 wt. % carbon dioxide, 20 to 35 wt. % ethylene, and 30 to 45 wt. % methane; ii) processing the aqueous stream to produce (a) a product stream containing 5 to 15 wt. % ethylene oxide, (b) a reabsorber overhead stream containing 20 to 50 wt. % ethylene, 10 to 30 wt. % methane, 1 to 10 wt. % argon, and 20 to 50 wt. % carbon dioxide; and iii) processing the EO absorber overhead stream in a processing unit to produce a carbonate flash gas stream containing 10 to 50 wt. % carbon dioxide, 5 to 45 wt. % ethylene, 5 to 10 wt. % methane, and 40 to 60 wt. % water. Embodiment 6 is the method of embodiment 5, wherein, in step (ii), the aqueous stream is processed in a reabsorber. Embodiment 7 is the method of embodiment 6, wherein the reabsorber includes a packed column that contains a water absorbent. Embodiment 8 is the method of any of embodiments 5 to 7, wherein the processing unit includes a carbon dioxide absorber configured to separate the EO absorber overhead stream to form a first recycle stream containing primarily ethylene and methane, collectively and a carbon dioxide rich stream containing primarily carbon dioxide, ethylene, methane, and water. The method also includes a flasher in fluid communication with the carbon dioxide absorber, wherein the flasher is configured to separate the carbon dioxide rich stream to produce the carbonate flash gas stream and a residual stream. In addition, the method includes a carbon dioxide stripper in fluid communication with the flasher and the carbon dioxide absorber, wherein the carbon dioxide stripper is configured to process the residual stream and to produce a lean carbonate solution to flow to the $CO_2$ absorber. Embodiment 9 is the method of embodiment 8, wherein the first recycle stream is recycled to the reactor. Embodiment 10 is the method of either of embodiments 8 or 9, wherein at least some of recycle gas stream is flowed to the carbon dioxide absorber, and/or the ethylene oxide absorber. Embodiment 11 is the method of any of embodiments 1 to 10, wherein the membrane separation unit includes one or more membrane modules, one or more housing pressure vessels, and one or more compressors. Embodiment 12 is the method of embodiment 11, wherein the membrane module includes a cellulose acetate/diacetate/triacetate membrane, a polyimide membrane, a perfluoro polymer membrane, a polysulfone membrane, a polycarbonate membrane, a poly (phenylene oxide) membrane, or combinations thereof. Embodiment 13 is the method of any of embodiments 1 to 12, wherein the combining includes flowing the reabsorber overhead stream and the carbonate flash gas stream to form a combined stream. The method further includes removing water from the combined stream in a knockout drum to form a de-watered stream, and compressing the de-watered stream to form the reclaim gas stream. Embodiment 14 is the method of embodiment 13, wherein the reclaim gas stream has a pressure in a range of 15 to 50 bar after compressing. Embodiment 15 is the method of any of embodiments 1 to 14, wherein the product stream further contains 85 to 95 wt. % water, and less than 1 wt. % carbon dioxide and ethylene, collectively. Embodiment 16 is the method of any of embodiments 1 to 15, wherein the product stream is further flowed to a purification column to form a high purity ethylene oxide product containing no less than 95 wt. % ethylene oxide. Embodiment 17 is the method of any of embodiments 1 to 16, wherein the product stream is fed to an ethylene glycol production reactor.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of producing ethylene oxide, the method comprising:
    reacting ethylene with a gas comprising oxygen in a reactor to produce a reactor effluent comprising ethylene oxide, carbon dioxide, unreacted ethylene, oxygen, methane, and argon;
    processing the reactor effluent to produce (a) a product stream comprising 5 to 15 wt. % ethylene oxide, (b) a reabsorber overhead stream comprising 20 to 50 wt. % ethylene and 10 to 30 wt. % methane, 1 to 10 wt. % argon, and 20 to 50 wt. % carbon dioxide and (c) a carbonate flash gas stream comprising 10 to 50 wt. % carbon dioxide, 5 to 45 wt. % ethylene, 5% to 10 wt. % methane, and 40% to 60% water;
    combining the reabsorber overhead stream and the carbonate flash gas stream to produce a reclaim gas stream;
    removing carbon dioxide and argon from the reclaim gas stream by a membrane separation unit to form a (1) recycle gas stream comprising ethylene and methane and (2) a gas stream comprising the removed carbon dioxide and the removed argon; and
    flowing the recycle gas stream to the reactor.

2. The method of claim 1, wherein the reacting is carried out in the presence of a catalyst comprising silver supported on silica, silica-alumina, or combinations thereof.

3. The method of claim 1, wherein the reacting is carried out at a reaction temperature of 200 to 300° C.

4. The method of claim 1, wherein the reacting is carried out at a reaction pressure of 33 to 35 bar.

5. The method of claim 1, wherein the processing comprises:
    i) processing the reactor effluent in an ethylene oxide (EO) absorber to produce (A) an aqueous stream comprising 2 to 5 wt. % ethylene oxide, 2 to 5 wt. % monoethylene glycol and (B) an EO absorber overhead stream comprising 2 to 15 wt. % carbon dioxide, 20 to 35 wt. % ethylene, and 30 to 45 wt. % methane;
    ii) processing the aqueous stream to produce (a) a product stream comprising 5 to 15 wt. % ethylene oxide, (b) a reabsorber overhead stream comprising 20 to 50 wt. % ethylene, 10 to 30 wt. % methane, 1 to 10 wt. % argon, and 20 to 50 wt. % carbon dioxide; and
    iii) processing the EO absorber overhead stream in a processing unit to produce a carbonate flash gas stream comprising 10 to 50 wt. % carbon dioxide, 5 to 45 wt. % ethylene, 5 to 10 wt. % methane, and 40 to 60 wt. % water.

6. The method of claim 5, wherein, in step (ii), the aqueous stream is processed in a reabsorber.

7. The method of claim 6, wherein the reabsorber comprises a packed column that contains a water absorbent.

8. The method of claim 5, wherein the processing unit comprises:
    a carbon dioxide absorber configured to separate the EO absorber overhead stream to form a first recycle stream comprising primarily ethylene and methane, collectively and a carbon dioxide rich stream comprising primarily carbon dioxide, ethylene, methane, and water;
    a flasher in fluid communication with the carbon dioxide absorber, wherein the flasher is configured to separate the carbon dioxide rich stream to produce the carbonate flash gas stream and a residual stream; and
    a carbon dioxide stripper in fluid communication with the flasher and the carbon dioxide absorber, wherein the carbon dioxide stripper is configured to process the residual stream and to produce a lean carbonate solution to flow to the $CO_2$ absorber.

9. The method of claim 8, wherein the first recycle stream is recycled to the reactor.

10. The method of claim 8, wherein at least some of recycle gas stream is flowed to the carbon dioxide absorber, and/or the ethylene oxide absorber.

11. A method of producing ethylene oxide, the method comprising:
    reacting ethylene with a gas comprising oxygen in a reactor to produce a reactor effluent comprising ethylene oxide, carbon dioxide, unreacted ethylene, oxygen, methane, and argon;
    processing the reactor effluent to produce (a) a product stream comprising 5 to 15 wt. % ethylene oxide, (b) a reabsorber overhead stream comprising 20 to 50 wt. % ethylene and 10 to 30 wt. % methane, 1 to 10 wt. % argon, and 20 to 50 wt. % carbon dioxide and (c) a carbonate flash gas stream comprising 10 to 50 wt. % carbon dioxide, 5 to 45 wt. % ethylene, 5% to 10 wt. % methane, and 40% to 60% water;
    combining the reabsorber overhead stream and the carbonate flash gas stream to produce a reclaim gas stream;
    removing carbon dioxide and argon from the reclaim gas stream by a membrane separation unit to form a (1) recycle gas stream comprising ethylene and methane and (2) a gas stream comprising the removed carbon dioxide and the removed argon; and
    flowing the recycle gas stream to the reactor, wherein the membrane separation unit comprises a membrane module, wherein the membrane module comprises a cellulose acetate/diacetate/triacetate membrane, a perfluoro polymer membrane, a polysulfone membrane, a polycarbonate membrane, a poly (phenylene oxide) membrane, or combinations thereof.

12. The method of claim 11, wherein the membrane module comprises a cellulose acetate/diacetate/triacetate membrane.

13. The method of claim 1, wherein the combining comprises:
    flowing the reabsorber overhead stream and the carbonate flash gas stream to form a combined stream;

removing water from the combined stream in a knockout drum to form a de-watered stream; and compressing the de-watered stream to form the reclaim gas stream.

14. The method of claim 11, wherein the membrane module comprises a poly (phenylene oxide) membrane.

15. The method of claim 1, wherein the product stream further comprises 85 to 95 wt. % water, and less than 1 wt. % carbon dioxide and ethylene, collectively.

16. The method of claim 1, wherein the product stream is further flowed to a purification column to form a high purity ethylene oxide product comprising no less than 95 wt. % ethylene oxide.

17. The method of claim 11, wherein the membrane module comprises a polycarbonate membrane.

18. The method of claim 11, wherein the membrane module comprises a perfluoro polymer membrane.

19. The method of claim 11, wherein the membrane module comprises a polysulfone membrane.

* * * * *